United States Patent [19]

Halvorsen

[11] 4,432,369

[45] Feb. 21, 1984

[54] ELECTROMAGNETIC SENSOR HAVING THREE ELECTRODES FOR MEASURING SIGNALS INDICATIVE OF A BIOLOGIC CONDITION

[75] Inventor: Kenneth G. Halvorsen, San Clemente, Calif.

[73] Assignee: Medi-Tech, Incorporated, Watertown, Mass.

[21] Appl. No.: 299,628

[22] Filed: Sep. 4, 1981

[51] Int. Cl.$^3$ .............................................. A61B 5/02
[52] U.S. Cl. ................................... 128/653; 128/700; 128/692; 128/733
[58] Field of Search ................ 128/642, 653, 691–692, 128/700, 733, 780

[56] References Cited

U.S. PATENT DOCUMENTS

| | | | |
|---|---|---|---|
| 3,717,031 | 2/1973 | Biscar | 128/692 |
| 3,838,683 | 10/1974 | Kolin | 128/692 |
| 4,036,215 | 7/1977 | Doll | 128/692 |

Primary Examiner—Kyle L. Howell
Assistant Examiner—Francis J. Jaworski

[57] ABSTRACT

An electromagnetic sensor for measuring signals indicative of a biologic condition in a body channel such as a blood vessel, throat, and the like, comprises a loop-shaped flat frame with laterally compressible and expansible sides, first and second electrodes mounted at opposite sides of the frame, and a third electrode mounted at one side of the frame near the first electrode. Lead wires connected to the electrodes are arranged in a trifilar array and secured to the frame. The lead wires are connected to circuitry comprising a 180° signal inverter for inverting signals picked up at one side of the channel or across the channel to suppress like signals picked up across the channel or at one side of the channel respectively, leaving only desired third signals indicative of the biologic condition to be measured which may be velocity of fluid flow, an esophageal muscular condition, diameter of a blood vessel, etc.

8 Claims, 3 Drawing Figures

ELECTROMAGNETIC SENSOR HAVING THREE ELECTRODES FOR MEASURING SIGNALS INDICATIVE OF A BIOLOGIC CONDITION

This invention relates to systems for measuring blood flow and electromyographic measurements in body channels using probes carrying electrodes, and more particularly concerns means for eliminating unwanted electrocardiographic signals which interfere with or mask desired signals.

It is known to employ a probe having a resilient collapsible frame carrying bifilar wires with spaced electrodes for making blood flow measurements, as described in U.S. Pat. No. 3,757,773 issued to A. Kolin, Sept. 11, 1973. In a conventional electromagnetic blood flow measurement system, the blood velocity is proportional to a voltage generated across a blood vessel and picked up by the electrodes in the blood vessel.

It is also known to provide a probe with three electrodes for nulling out quadrature electromotive force which is independent of blood flow and which is in quadrature phase with the useful flow signal, as described in U.S. Pat. No. 3,717,031 issued to J. P. Biscar on Feb. 20, 1973.

It has been discovered that when blood flow measurements are made near a patient's heart, the electrodes pick up both a blood velocity signal and a strong in phase electrocardiographic (EKG) signal. This results in incorrect measurements of blood velocity. This undesired EKG signal cannot be neutralised by the methods described in the prior patents referred to above.

The present invention is directed at overcoming this undesirable condition by modifying the probe and associated electrical circuit. According to the invention a probe is provided having trifilar wires with three electrodes. Two electrodes of the probe are connected respectively to two of the wires and are located at opposite sides of the probe. The third electrode is connected to a third wire near one of the two electrodes at one side of the frame of the probe. The blood velocity signal is picked up with the two electrodes positioned across the blood vessel. These two electrodes also pick up an undesired in-phase EKG signal. The third electrode on the third wire is located on the same side of the probe as the first electrode. The signal from the third electrode and the first electrode pick up a strong EKG signal generated at the one side of the probe and blood vessel.

Further in accordance with the invention, the signals are fed to external circuitry where the EKG signal, picked up by the first and third electrodes is neutralized or suppressed and the desired blood velocity signal free from the interfering EKG signal is obtained.

The invention is applicable to electromyographic (EMG) measurements. For example when a trifilar wire probe according to the invention is inserted into a patient's throat, the EMG signal generated by esophageal muscles will be picked up at one side of the esophagus by the two closely located electrodes at one side of the frame of the probe. These two electrodes also pick up a strong unwanted in-phase EKG signal. The two electrodes at opposite sides of the probe located at opposite sides of the esophagus pick up a strong EKG signal and do not pick up the EMG signal. The signals are fed to an external circuit where the EKG signal is suppressed or neutralized in obtaining the desired EMG signal.

It is therefore a principal object of the present invention to provide an electromagnetic system for measuring biological conditions in a body channel.

It is another object of the present invention to provide an electromagnetic system for measuring biological conditions in a body channel near a patients heart and suppress or neutralize the bodys EKG signal therefrom.

It is yet another object of the present invention to provide an electromagnetic system for measuring electromyographic signals generated by the esophagus muscle and suppress or neutralize the bodys EKG signal therefrom.

These and other objects and many of the attendant advantages of this invention will be readily appreciated as the same becomes better understood by reference to the following detailed description when considered in connection with the accompanying drawings in which.

Figure 1:
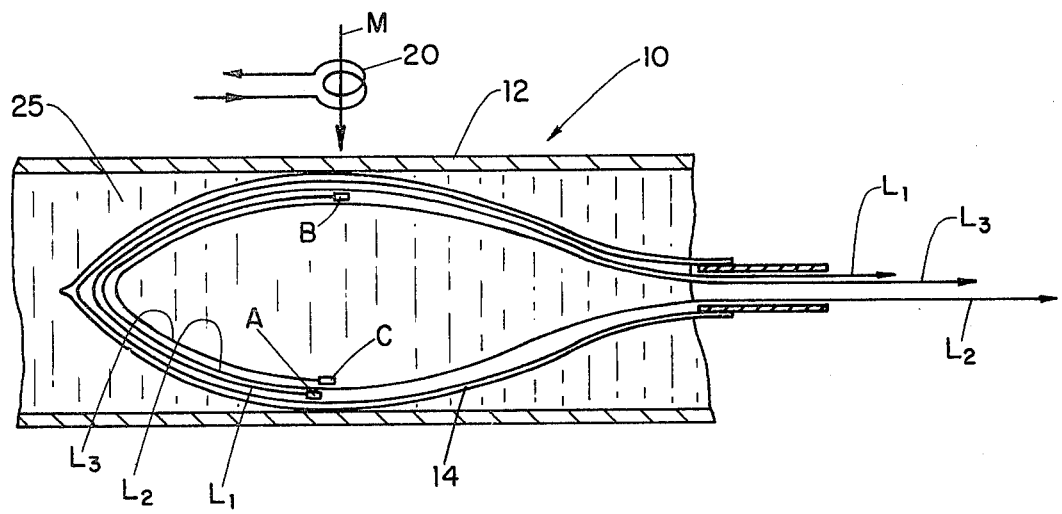
FIG. 1 is a schematic representation of an electromagnetic catheter-type probe embodying features of the invention.

Referring now to the drawings wherein like reference characters designate like or corresponding parts throughout, there is illustrated in FIG. 1, a catheter-type probe generally designated as reference numeral 10 inserted and expanded inside a blood vessel 12. The probe comprises an expansible frame 14 carrying three insulated looped lead wires $L_1$, $L_2$, and $L_3$ in trifilar array secured to and extending arround the frame 14. On opposite sides of the frame 14 located at opposite sides of the vessel 12 are two electrodes A and B secured to wires $L_1$ and $L_2$ respectively. A third electrode C is connected to lead wire $L_3$ at one side of the frame 14 near the electrode A at one side of the blood vessel 12. A suitable generator 20 of a magnetic field M is located near the probe so that the field M is orthogonal to the direction of blood flow. As blood 25 flows through the blood vessel 12, the electrodes A and B pick up a signal whose voltage is proportional to blood velocity and an in-phase undesired EKG signal. The electrode C picks up a similar EKG signal.

Figure 2:
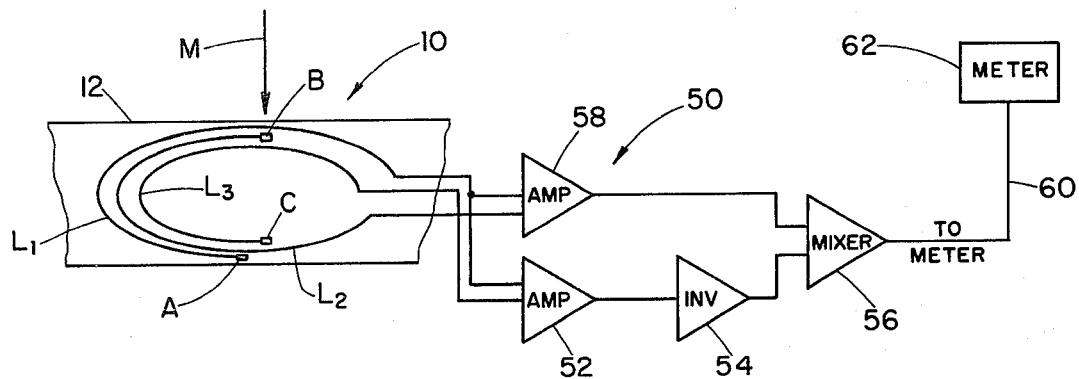
FIG. 2 is a schematic diagram of the probe of FIG. 1 and associated circuitry used to suppress undesired EKG signals in blood velocity measurement.

FIG. 2 shows a circuit 50 external of the vessel 12 and connected to the wires $L_1$, $L_2$, $L_3$, of the probe 10 inside the vessel 12. The circuit 50 includes a first amplifier 52 connected to a 180° inverter 54 connected to a mixer circuit 56. The strong EKG signal picked up by the electrodes A and C are fed to the amplifier 52 and then to the inverter 54, where the EKG signal is inverted and applied to the input of the mixer circuit 56. The combined in-phase EKG and blood velocity signals picked up by the electrodes A and B are fed to a second amplifier 58 which is also connected to the mixer 56 where the undesired EKG signals are neutralised. At the output 60 of the mixer 56 appears the desired blood velocity signal free of the interfering EKG signals, and this signal is applied to a meter 62 connected to the mixer 56.

Figure 3:
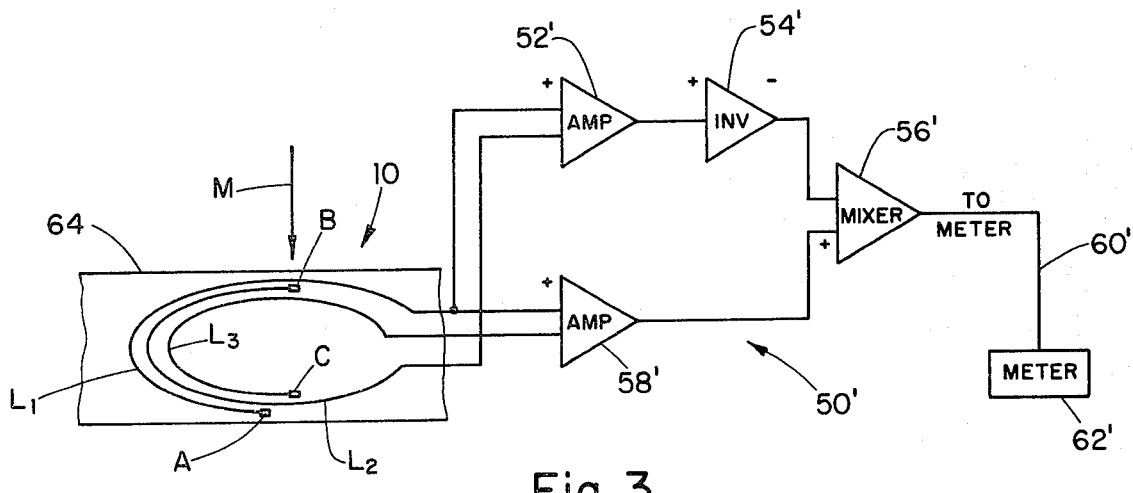
FIG. 3 is a schematic diagram of another probe similar to that of FIGS. 1 and 2 connected to circuitry similar to that of FIG. 2 in such manner as to suppress undesired EKG signals in EMG measurement.

FIG. 3 shows a probe 10 used for making EMG measurements in a throat 64 of a patient. The probe 10 has the three lead wire loops $L_1$, $L_2$, $L_3$, in a trifilar array, carrying electrodes A, B, and C respectively and connected to external circuitry 50'. Electrodes A and C are located close to each other at one side of the probe 10. Electrode B is located at the other side of the probe 10. Electrodes A and C at one side of the probe pick up combined in-phase EMG and EKG signals. These are applied to an amplifier 58' and mixer 56'. Electrodes A and B at opposite sides of the probe 10 pick up a strong EKG signal which is applied to an amplifier 52', an inverter 54', and then fed to a mixer 56'. At an output 60' of the mixer 56' appears the desired EMG signal free from the undesired neutralised EKG signals. The EMG signal is applied to a meter 62'.

It will be apparent from the foregoing that both systems described invert one of two EKG signals picked up at one side of a channel and at opposite sides of the channel respectively to suppress to EKG signals and leave a remaining desired signal indicative of a biologic condition.

The invention makes possible more accurate and reliable measurements of blood velocity signals, electromyographic signals, and other signals indicative of certain conditions in body channels.

It should be understood that the foregoing relates to only a limited number of preferred embodiments of the invention which have been by way of example only and that it is intended to cover all changes and modifications of the examply of the invention herein chosen for the purposes of the disclosure, which do not constitute departures from the spirit and scope of the invention.

What is claimed is:

1. An electromagnetic sensor for measuring signals indicative of a biologic condition in a body channel, comprising:
   a loop-shaped flat frame having an open end and opposite closed end, and having sides laterally compressible and expansible in the plane of said frame for insertion into said channel in compressed form and expansion therein to contact opposite sides of said channel;
   first and second electrodes mounted at opposite sides of said frame and disposable at opposite sides of said channel when said frame is expanded therein for picking up signals generated across said channel;
   a third electrode mounted at one side of said frame adjacent said first electrode for picking up signals generated at said one side of said channel;
   magnetic means for generating a magnetic field orthogonal to said frame within said channel in the region of said electrodes;
   wires connected to said electrodes respectively and carried by said frame, and extending out of said open end of said frame, whereby multiple signals picked up by said electrodes appear on said wires; and
   circuit means connected to said wires externally of said frame to receive said picked up signals, said circuit means being adapted to mix first signals picked up across said first and second electrodes, with second signals picked up at said first and third electrode and neutralize one of said first and second signals, leaving only third signals to be passed to a signal measuring means.

2. An electromagnetic sensor as defined in claim 1, wherein said circuit means comprises:
   a 180° signal inverter connected in circuit with said first and third electrodes for inverting said second signals picked up at said one side of said channel; and
   a signal mixer connected in circuit with said inverter and said first and second electrodes for mixing said inverted signals with said first signals picked up across said channel to neutralize said first and second signals, leaving only said third signals for measuring velocity of fluid flow through said channel.

3. An electromagnetic sensor as defined in claim 2, wherein said lead wires are arranged in a trifilar array secured to and extending around said frame for efficiently picking up signals indicative of said velocity of fluid flow in said channel.

4. An electromagnetic sensor as defined in claim 1, wherein said first and second signals are electrocardiographic signals, and wherein said third signals are in-phase with said first signals and are proportional in voltage to velocity of fluid flow through said channel.

5. An electromagnetic sensor as defined in claim 1, wherein said circuit means comprises:
   a 180° signal inverter connected in circuit with said first and second electrodes for inverting said first signals picked up across said channel; and
   a signal mixer connected in circuit with said inverter and said first and third electrodes for mixing said inverted signals with said second signals on said one side of said channel to neutralize said first and second signals leaving only said third signals indicative of a condition at said one side of said channel.

6. An electromagnetic sensor as defined in claim 5, wherein said first and second signals include cardiographic signals picked up across said channel and at said one side of said channel respectively, and wherein said third signals are electromyographic signals picked up only at said one side of said channel and in phase with said second signals.

7. An electromagnetic sensor as defined in claim 1, wherein said lead wires are arranged in a trifilar array secured to said frame for contraction and expansion with said frame in said channel.

8. An electromagnetic sensor as defined in claim 7, wherein said trifilar array of lead wires extends around said frame for efficiently picking up signals at said electrodes.

* * * * *